United States Patent [19]

Roman

[11] 4,045,559

[45] Aug. 30, 1977

[54] USE AS INSECTICIDES OF ESTERS OF NITRO(TETRAHYDRO-2H-1,3-THIAZIN-2-YLIDENE)ACETIC ACIDS

[75] Inventor: Steven A. Roman, Oakdale, Calif.

[73] Assignee: Shell Oil Company, Houston, Tex.

[21] Appl. No.: 665,982

[22] Filed: Mar. 11, 1976

Related U.S. Application Data

[63] Continuation-in-part of Ser. No. 554,371, March 3, 1975, Pat. No. 3,962,234, which is a continuation-in-part of Ser. No. 468,125, May 8, 1974, abandoned.

[51] Int. Cl.$^2$ .......................... A01N 9/00; A01N 9/12
[52] U.S. Cl. .................................................. 424/246
[58] Field of Search .......................... 260/243; 424/246

[56] References Cited

U.S. PATENT DOCUMENTS

| 3,933,809 | 1/1976 | Powell | 424/246 |
| 4,015,001 | 3/1977 | Powell | 424/246 |

OTHER PUBLICATIONS

Chem. Pharm. Bull. 2097-2101, (1972), Hirai et al., "Synthesis and Reactions of 2-Substituted Thiazolidenes".

*Primary Examiner*—Albert T. Meyers
*Assistant Examiner*—D. W. Robinson

[57] ABSTRACT

Use as insecticides of esters of nitro(tetrahydro-2H-1,3-thiazin-2-ylidene)acetic acids.

2 Claims, No Drawings

USE AS INSECTICIDES OF ESTERS OF NITRO(TETRAHYDRO-2H-1,3-THIAZIN-2-YLIDENE)ACETIC ACIDS

This application is a continuation-in-part of copending application Ser. No. 554,371, filed March 3, 1975, issued June 8, 1976, as U.S. Pat. No. 3,962,234 which is a continuation-in-part of application Ser. No. 468,125, filed May 8, 1974, now abandoned.

DESCRIPTION OF THE INVENTION

It has been found that useful insecticidal activity is possessed by certain esters of nitro(tetrahydro-2H-1,3-thiazin-2-ylidene)acetic acids. These esters are resonance hybrids, the principle forms contributing thereto being described by the formulae

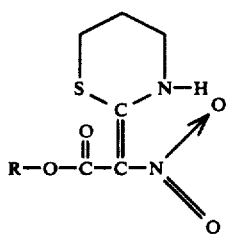

(A)

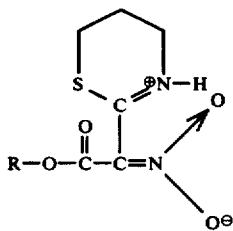

(B)

wherein the symbols have the respective meaning set out hereinafter.

These compounds also can exist in the corresponding tautomeric enol form which can be described by the formula

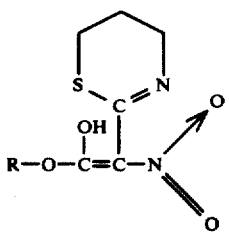

(C)

The resonance hybrids may exist as either of two geometric (cis-trans) isomers, depending upon the spatial relationship of the moieties about the bond between the carbon atom of the nitromethylene moiety and the ring carbon atom to which it is joined.

The enol form (Form C) can be designated as a 1-R-O-2-nitro-2-(5,6-dihydro-4H-1,3-thiazin-2-yl)vinyl alcohol. The left-hand form of the resonance hybrid (Form A) can be designated as an ester of nitro(tetrahydro-2H-1,3-thiazin-2-ylidene)acetic acid. The right-hand form (Form B) can be designated as an 2-(R-oxycarbonyl-aci-nitromethyl)-5,6-dihydro-4H-1,3-thiazinium hydroxide inner salt.

In this specification, for the sake of simplicity, these compounds will be referred to generally as esters of nitro(tetrahydro-2H-1,3-thiazin-2-ylidene)acetic acid. This terminology is intended to include all of the contributors to the resonance hybrid, the geometric isomers and the enol form, as well as mixtures thereof.

In these compounds, R contains up to thirty carbon atoms and is alkyl, alkenyl, alkynyl, cycloalkyl, cycloalkylalkyl, alkadienyl, haloalkyl, haloalkenyl, mono- and poly-(alkoxy)alkyl, alkylthioalkyl, phenylthioalkyl, benzylthioalkyl, cyanoalkyl, hydroxyalkyl, alkylsulfinylalkyl, alkylsulfonylalkyl, phenyl or phenalkyl or either substituted on the ring by one to two of one or more of halogen, nitro, cyano, alkyl, phenyl, alkoxy or phenoxy; is aminoalkyl, $-(CH_2)_m-NR^3R^4$, wherein $m$ is one or two, $R^3$ is alkyl, cycloalkyl, alkenyl, phenyl or phenylalkyl, and $R^4$ is hydrogen or one of the moieties represented by $R^3$; or is $-(CH_2)_n-R^5$, wherein $n$ is zero, one or two, and $R^5$ is a heteromonocyclic moiety of from five to six atoms in the ring, containing in the ring carbon atoms and one to two of oxygen (—O—), sulfur (—S—) and nitrogen (=N— or —NH—) bonded to carbon in the ring.

Preferably, the moiety represented by R contains no more than ten carbon atoms and when aliphatic may be of straight-chain or branched-chain configuration. The preferred aryl moieties are optionally substituted phenyl. The preferred aminoalkyl moieties are dialkylaminomethyl and -ethyl. The preferred aralkyl moieties are optionally-substituted phenylmethyl. Preferred heterocyclic ($R^5$) moieties are furanyl, tetrahydrofuranyl, dioxolanyl, thienyl, thiopyranyl, pyridinyl, pyrrolidinyl-, morpholinyl, and their $R^5$-methyl- counterparts.

Also, the invention includes salts of the compounds described above, both simple salts and inner salts of the formula:

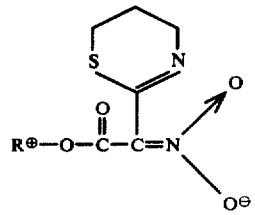

such as ammonium and pyridinium salts.

The contemplated salts include alkali metal salts, ammonium salts, pyridinium salts and amine salts generally, and particularly salts of alkyl- and alkanolamines, and polyamines. Included are the salts of mono-, di- and trialkyl, alkanol, alkenyl and mono- and poly- (alkoxy)alkylamines, and polyamines in which each alkyl, alkenyl, alkanol, or alkoxyalkyl moiety contains from one to twenty carbon atoms or more including, but not necessarily limited to, one or more of dimethylamine, diethanolamine, trimethylamine, oleyl propylenediamine, n-dodecylamine, n-tetradecylamine, n-hexadecylamine, n-octadecylamine, heptylamine, triethanolamine, tert-$C_{11-14}$ and tert-$C_{18-24}$ primary amines, oleylamine, coco amine, hydrogenated tallow amine, tallow amine, soya amine, dicoco amine and di(hydrogenated tallow) amines, dimethyl hexadecylamine, dimethyl octadecylamine, dimethyl coco amine, dimethyl soya amine, N-coco propylenediamine, N-soya propylenediamine, N-tallow propylenediamine, and the like.

For illustration, preparation of typical species esters of the genus is described in the examples included hereinafter. Other typical, illustrative species of this genus of esters of nitro(tetrahydro-2H-1,3-thiazine-2-ylidene)acetic acids include those wherein the symbols represent the following moieties, this manner of naming these species being accurate, yet pointing out the differences between the different species more clearly than if the entire, complicated name of each species were to be given;

R =
  3-cyanopropyl
  cyclobutyl
  cholesteryl
  farnesyl
  (1-methyl-2-piperidinyl)methyl
  (1-methyl-2-pyrrolyl)methyl
  (1-methyl-2-imidazolyl)methyl
  2-thiazolylmethyl
  2-oxazolylmethyl
  2-pyrimidinylmethyl
  2-(1-pyrrolidinyl)ethyl
  benzylideneaminomethyl
  2-(dimethylamino)ethyl
  2-(methylsulfonyl)ethyl
  2-(diphenylamino)ethyl
  1-methyl-3-piperidinyl
  1-benzyl-3-piperidinyl
  (2,2,3,3-tetramethylcyclopropyl)methyl Compounds of this invention can be prepared by several general procedures. In most cases it will be found that the most effective procedure is the base-promoted transesterification of an alkyl ester ($R^1$ = alkyl) which can be prepared by the zinc ion-catalyzed reaction of 5,6-dihydro-2-(methylthio)-4H-1,3-thiazine (A. F. McKay et al., J. Am. Chem. Soc. 80, 3339 (1950) with an alkyl nitroacetate (S. Zen, et al., Kogyo Kagaku Zasshi, 74, 70 (1971).

It will be found in some cases that it will be most convenient to use the methyl or ethyl ester.

The ester interchange follows the conventional base-catalyzed reaction of an ester with the alcoholate of the appropriate alcohol. According to one technique, the interchange can be effected by treating the alkyl ester with an excess of the appropriate alcohol in the presence of two equivalents of an alkali metal (one equivalent of the metal converts the alcohol to the alcoholate, while the other equivalent neutralizes the acidic thiazine ester products). Use of a small to moderate (5-10%) excess of the metal may be desirable in some cases. Generally, the reaction can be effected at temperatures of about 20°-100°.

Alternatively, the metal alcoholate can be prepared and reacted with the ester in an aprotic low-dielectric solvent such as tetrahydrofuran. This may be done by treating the appropriate alcohol in the solvent with an alkali metal hydride, then adding the ester, also in the solvent. The reaction of the alcohol and hydride usually is exothermic so that cooling is usually needed to control the temperature of the reaction mixture. Reaction of the alcoholate with the ester ordinarily can be conducted at room temperature.

With either technique, recovery of the product is most effectively attained in most cases by quenching the final reaction mixture in water, treating the aqueous mixture with a suitable solvent such as ether to remove the solvent alcohol and other neutral organic species, then acidifying the aqueous phase. In some cases, the product ester crystallizes out of the water; in other cases, it can be recovered by extracting the water-phase with a suitable water-insoluble solvent such as methylene chloride or ethyl ether.

Compounds of this invention also can be prepared by treating tetrahydro-(2-nitromethylene)-2H-1,3-thiazine with a 1-(R-oxycarbonyl)-3-methylimidazolium chloride by the method described by E. Guibe-Jampel, et al., Bull. Soc. Chim. Fr. 1973 (3) (Pt. 2), pp. 1021-7. According to this method, the imidazolium chloride is prepared by treating 1-methylimidazole with the appropriate chloroformate, R-O-C(O)-Cl, preferably in a suitable solvent and at a low temperature, for example, about 0° C. A suitable general method for conducting this procedure comprises adding a solution of the chloroformate in tetrahydrofuran slowly (e.g., dropwise) to a cold (e.g., 0°) solution of the N-methylimidazole in the same solvent, stirring the cold mixture for a period of from about 15 minutes to one hour to ensure complete reaction, then adding to that stirred cold mixture a solution of the thiazine, then warming the stirred mixture to a temperature of from about room temperature to the reflux temperature, and stirring the warm mixture for a time to ensure complete reaction.

The desired product can be isolated from the crude reaction mixture and purified by conventional methods, such as filtration, extraction, crystallization and elution (chromatography). The use of this method for preparing compounds of this invention, and preparation of the thiazine precursor, are described in Example 66, hereinafter.

These procedures for preparing compounds of this invention are illustrated in the following examples of the preparation of particular species of such compounds. In all cases, the identity of the product and of any intermediate employed was confirmed by elemental analyses and by infrared and nuclear magnetic resonance spectrum analyses.

EXAMPLE 1

Ethyl nitro (tetrahydro-2H-1,3-thiazin-2-ylidene)acetate (1)

To a mixture of 235 g of 5,6-dihydro-2-(methylthio)-4H-1,3-thiazine and 2 g of zinc chloride at approximately 115° in a nitrogen atmosphere, 236 g of ethyl nitroacetate was added dropwise over a 1.5 hour period. The mixture was held at 110°-120° and the nitrogen atmosphere was maintained during the addition. When evolution of methyl mercaptan ceased after 45 minutes further stirring of the heated mixture, 1 g of zinc chloride was added to the stirred mixture at ca. 115°. After 1.25 hours an additional 1 g of zinc chloride was added and stirring of the mixture at ca. 115° was continued for 1.5 hours. The mixture then was poured into a cooled solution of 2/1 ether/isopropyl alcohol mixture. The crystallized product was collected, washed with ether and dried under reduced pressure to leave a tan solid, m.p.: 100°-102° which on recrystallization from methanol gave 1, as a pale yellow solid, m.p.: 105°-106°.

EXAMPLE 2

Methyl nitro (tetrahydro-2H-1,3-thiazin-2-ylidene)acetate (2)

2 was obtained from methyl nitroacetate as a pale yellow solid, m.p.: 107°–108° by a procedure analogous to that described in Example 1.

EXAMPLE 3

Propyl nitro (tetrahydro-2H-1,3-thiazin-2-ylidene)acetate (3)

0.5 g of sodium was dissolved in 50 ml of 1-propanol. To the solution was added 2.2 g of 2. After 2.5 hours of stirring at room temperature, the mixture was quenched in water and acidified with acetic acid to pH = 6. The aqueous mixture was extracted with methylene chloride and the methylene chloride extracts were washed with saturated sodium bicarbonate solution and with saturated salt solution. The organic phase was dried with magnesium sulfate and the solvent was removed under reduced pressure to leave a crystalline solid, m.p.: 42°–48°. Recrystallization of the solid from ether-hexane gave 3 as a pale yellow crystals, m.p.: 59°–60°.

EXAMPLE 4

Heptyl nitro(tetrahydro-2H-1,3-thiazin-2-ylidene)acetate (4)

1.5 g of sodium was dissolved in 50 ml of heptanol. To the resulting solution was added 6.6 g of 2. After 18 hours of stirring at room temperature, the mixture was quenched in water and washed with ether. The aqueous phase was acidified with acetic acid and extracted with ether. The combined extracts were washed with water, dried over anhydrous magnesium sulfate and treated with decolorizing carbon. Evaporation of the solvent left a residue which, when recrystallized from ether/hexane, gave 4 as an off-white powder, m.p.: 59°–60°.

EXAMPLE 5

4-chlorobenzyl nitro(tetrahydro-2H-1,3-thiazin-2-ylidene)acetate (5)

A solution of 4-chlorobenzyl alcohol in 100 ml of dry tetrahydrofuran was added dropwise to a cooled suspension of 3.0 g of sodium hydride (57% in mineral oil) in 50 ml of dry tetrahydrofuran. When evolution of hydrogen had ceased, 6.6 g of 2 was added all at once. After 18 hours at room temperature, the mixture was quenched in water and washed twice with ether. The aqueous phase was acidified with acetic acid. A yellow precipitate formed. On recrystallization from ethyl acetate/isopropyl alcohol, 5 was obtained as a yellow solid, m.p.: 119°–119.5°.

EXAMPLES 6–60

By ester exchange procedures analogous to that described in Examples 3, 4 and 5, the following additional esters of nitro(tetrahydro-2H-1,3-thiazin-2-ylidene)acetic acid were prepared from the appropriate alkali metal alcoholates:

| Example | Ester | Description: Solids of Indicated Color and Melting Point (° C) | |
| --- | --- | --- | --- |
| 6 | Isopropyl | Off-white | 93–94 |
| 7 | Isobutyl | Pale yellow | 64–65 |
| 8 | n-butyl | Yellow | 51–53 |
| 9 | Allyl | Yellow | 58–59.5 |
| 10 | 2-propynyl | Yellow | 116–117 |
| 11 | Pentyl | Pale yellow | 48–48.5 |
| 12 | 2,2-dimethylpropyl | Yellow | 48.5–50 |
| 13 | Octyl | Yellow | 82–83 |
| 14 | 2-butenyl | Yellow | 95–96 |
| 15 | 2,2,2-trifluoroethyl | Yellow | 89–90 |
| 16 | 2-methoxyethyl | Yellow | 75–76 |
| 17 | Cyclopentyl | Beige | 91–91.5 |
| 18 | 2-furanylmethyl | Yellow | 93–94 |
| 19 | 2-butynyl | Yellow | 140–141 |
| 20 | 4-methoxybenzyl | White | 87.5–89 |
| 21 | 3-butynyl | Pale yellow | 90–91 |
| 22 | 3,7-dimethyl-2,6-octadienyl | Pale yellow | 66–67 |
| 23 | 1-methyl-2-propynyl | Yellow | 91–92 |
| 24 | 1-methyl-2-propenyl | Yellow | 59–61 |
| 25 | Hexyl | Pale yellow | 66.5–67.5 |
| 26 | 1-naphthalenylmethyl | Yellow | 124–124.5 |
| 27 | Tetrahydro-2-furanylmethyl | Pale yellow | 55–57 |
| 28 | 2-ethoxyethyl | Yellow | 15 |
| 29 | 2,2-dimethyl-1,3-dioxolan-4-ylmethyl | White | 107.5–108.5 |
| 30 | 2-(2-methoxyethoxy)ethyl | Pale yellow | 54–55 |
| 31 | 3-phenoxybenzyl | White | 126–126.5 |
| 32 | 3-butenyl | Pale yellow | 55–56 |
| 33 | 4-cyanobenzyl | Pale yellow | 179 ∝ 180 |
| 34 | Cyclopropylmethyl | Pale yellow | 93.5–94 |
| 35 | 2,4-dichlorobenzyl | Pale yellow | 161–161.5 |
| 36 | 1-cyclopropylethyl | Pale yellow | 62–63 |
| 37 | 2-(1-naphthylenyl)ethyl | Pale yellow | 99–99.5 |
| 38 | 2-naphthalenylmethyl | Yellow | 130–131 |
| 39 | (trans)-3-chloro-2-propenyl | Pale Yellow | 70–71.5 |
| 40 | (cis-3-chloro-2-propenyl | Yellow | 62–64 |
| 41 | 2-methylthioethyl | Pale Yellow | 72–73 |
| 42 | 2-thienylmethyl | Yellow | 75–76 |
| 43 | isobornyl | Off-white | 132–133 |
| 44 | 2-(dimethylamino)ethyl | Yellow | 94.5–95.5 |
| 45 | cyclohexylmethyl | Yellow | 90.5–91 |
| 46 | tetrahydro-2H-thiopyran-3-yl | Yellow | 106–107 |
| 47 | menthyl | Yellow | 157.5–158.5 |
| 48 | 3-chloropropyl | Yellow | 69–70 |
| 49 | 2-hydroxyethyl | Yellow | 96–97 |
| 50 | 2-pyridinylmethyl | Yellow | 104–105 |
| 51 | norbornyl | | 92–93 |
| 52 | 3-chloro-2-propenyl (mixture of isomers) | Yellow | 49–56 |
| 53 | 2-butoxyethyl | Yellow | <20 |
| 54 | 2-(4-morpholinyl)ethyl | Yellow | 91.5–92.5 |
| 55 | 2-(2-oxo-1-pyrrolidinyl)ethyl | Yellow | 117–118 |
| 56 | 2-(butylthio)ethyl | Yellow liquid | boiling point not determined |
| 57 | 2-(ethylthio)ethyl | Yellow | 70–71 |
| 58 | 2-(phenylthio)ethyl | Off-white | 70–71 |
| 59 | 3-(methylthio)propyl | Yellow | <20 |
| 60 | 3-pyridinylmethyl | Yellow | 97.5–98.5 |

EXAMPLE 61

2-methylsulfinylethyl nitro(tetrahydro-2H-1,3-thiazin-2-ylidine)acetate (61)

3.3 g of sodium periodate was added to a slurry of 4.0 g of 41 in 20 ml of acetone. The reaction was slightly exothermic. The mixture was stirred for 4.25 hours, then filtered. The solid phase was washed with methylene chloride and the layers were separated. The organic phase was dried, filtered and stripped of solvent under reduced pressure to give a yellow oil. This was boiled with ethyl acetate. The ethyl acetate phase was separated from an insoluble oil, cooled and filtered to give 61, as a yellow solid, m.p.: 91°–92°.

EXAMPLE 62

Phenylmethyl nitro(tetrahydro-2H-1,3-thiazin-2-ylidene)acetate (62)

62 was prepared as a yellow solid, m.p.: 78°-79° from benzyl nitroacetate by a procedure analogous to that described in Example 1.

EXAMPLE 63

Sodium salt of 5 (63)

350 g of 4-chlorobenzyl alcohol was treated with 19.2 g of sodium hydride in tetrahydrofuran at 0°. The mixture was allowed to warm to room temperature and was added all at once to 43.6 g of 2. The mixture was stirred overnight at room temperature. The tetrahydrofuran then was evaporated under reduced pressure, the residue poured into water and the mixture was extracted with ether (a precipitate formed). The solid was filtered off and recrystallized from a 2:2:1 mixture of ethanol, ethyl acetate and methanol to give 63 as a white solid, m.p. (with decomposition): 215°.

EXAMPLE 64

2-(phenylmethylthio)ethyl nitro(tetrahydro-2H-1,3-thiazin-2-ylidene)acetate (64)

1.8 g of 41, 5 ml of benzylbromide and 25 ml of acetone were mixed and the mixture stirred at reflux temperature for seven days. The mixture then was cooled and the solvent stripped under reduced pressure, to leave an oil, which was filtered through Florisil with the aid of methylene chloride, which was stripped to leave 64, as a yellow oil, boiling point not determined.

EXAMPLE 65

3-iodopropyl nitro(tetrahydro-2H-1,3-thiazin-2-ylidene)acetate (65)

2.1 g of 48, 3 g of sodium iodide and 35 ml of acetone were mixed and the mixture refluxed overnight. The reaction mixture then was quenched in water, the resulting mixture extracted with methylene chloride. The extracts were washed with water and dried (MgSO$_4$) to give an oil, which was triturated with ether overnight, then diluted with hexane, resulting in a bright yellow precipitate. This was recrystallized from ether to give 48, as a yellow solid, m.p.: 58°-60°.

EXAMPLE 66

Phenyl nitro(tetrahydro-2H-1,3-thiazin-2-ylidene)acetate (66)
Ethyl nitro(tetrahydro-2H-1,3-thiazin-2-ylidene)acetate (A)

To a mixture of 235 g of 5,6-dihydro-2-(methylthio)-4H-1,3-thiazine (A. F. McKay, et al., J. Am. Chem. Soc., 80, 3339 (1958)) and 2 g of zinc chloride, at approximately 115° in a nitrogen atmosphere, 263 g of ethyl nitroacetate (S. Zea, et al., Kogyo Kagaku Zasshi, 74, 70 (1971)) was added dropwise over a 1.5 hour period. The mixture was held at 110°-120°. When evolution of methyl mercaptan ceased after 45 minutes further stirring of the heated mixture, 1 g of zinc chloride was added and the mixture was stirred at about 115° for 1.25 hours. An additional 1 g of zinc chloride then was added and stirring of the mixture at about 115° was continued for 1.5 hours. The mixture then was poured into a cooled solution of 2/1 ether/isopropyl alcohol mixture. The crystallized product was collected, washed with ether and dried under reduced pressure to leave a tan solid, m.p. 100°-102°, which on recrystallization from methanol gave A as a pale yellow solid, m.p. 105°-106°.

Tetrahydro-2-(nitromethylene)-2H-1,3-thiazine (B)

2.3 g of A was added to 10 ml of 20% aqueous sodium hydroxide and the mixture was stirred at room temperature for 12 hours. The resulting solution was treated dropwise with 3.5 g of acetic acid. The addition was accompanied by vigorous gas evolution. The resulting mixture was extracted with methylene chloride and the extract was dried (magnesium sulfate) and concentrated under reduced pressure to give B as a pale yellow solid, m.p. 76°-78°.

66

A solution 17.2 g of phenyl chloroformate in 25 ml of tetrahydrofuran was added dropwise to a solution of 9.09 g of 1-methylimidazole in 75 ml of tetrahydrofuran, the temperature of the reaction mixture being kept below 10° by means of an ice bath. Thirty minutes after the addition was completed, a solution of 16.0 g of B in 150 ml of tetrahydrofuran was added rapidly dropwise. The stirred mixture then was allowed to warm to room temperature and stirred for two days. The mixture was extracted with methylene chloride, the extracts washed with water, dried (MgSO$_4$) and the solvent stripped off to give an oil. The oil was triturated first with a mixture of methanol and water, then with a cold mixture of methanol and ether to give as residue an orange-yellow solid, which on recrystallization from ethanol gave 66, as a pale yellow solid, m.p.: 95°-6°.

EXAMPLE 67

1-methyl-3-((nitro(tetrahydro-2H-1,3-thiazin-2-ylidene)acetoxy)methyl pyridinium iodide (67)

1 g of 60 and 10 ml of methyl iodide in 25 ml of methanol were refluxed for 1 hour. Then an additional 10 ml of methyl iodide was added and the mixture refluxed for an additional 15 minutes. Most of the solvent was stripped under reduced pressure and the residue was triturated with ether to give a pale yellow powder. This was recrystallized from methanol to give 67, as a pale yellow powder, m.p. (with decomposition): 163°-165°.

EXAMPLES 68 AND 69:

In a similar manner were prepared 1-methyl-2-((nitro(tetrahydro-2H-1,3-thiazin-2-ylidene)acetyloxy)methyl)pyridinium iodide (68), as a pale yellow solid, m.p.: 159° (with decomposition), and N,N,N-trimethyl-2-(nitro-(tetrahydro-2H-1,3-thiazin-2-ylidene)acetyloxy)ethanaminium iodide (69), as a yellow solid, m.p.: 155°-156° (with decomposition).

EXAMPLE 70

3-(((5,6-dihydro-4H-1,3-thiazin-2-yl)aci-nitroacetyloxy)methyl)-1-methyl pyridinium hydroxide, inner salt (70)

A slurry of 1.5 g of 67 in 100 ml of methanol was treated dropwise with 0.85 g of thallium ethoxide in 25 ml of ethanol. A yellow precipitate formed. After 15 minutes stirring, the mixture was filtered to give a red filtrate. The solvent was stripped from the filtrate and the residue was triturated with acetonitrile to give a salmon-colored powder. Recrystallization from a mixture of acetonitrile, methanol and ether gave 70 as a salmon-colored solid, m.p.: 145.5° (with decomposition).

EXAMPLES 71–87

The following additional esters of nitro(tetrahydro-2H-1,3-thiazin-2-ylidene)acetic acid also were prepared from the appropriate alkali metal alcoholates by ester exchange procedures described in Examples 3, 4 and 5:

| Example | Ester | Description: Solids of indicated color and melting point (° C) | |
|---|---|---|---|
| 71 | 3-(dimethylamino)propyl | yellow | 44 – 45 |
| 72 | 4-methylbenzyl | pale yellow | 107 – 107.5 |
| 73 | 3-chlorobenzyl | yellow | 103.5 – 104.5 |
| 74 | 2-(octylthio)ethyl | yellow | 47 –48 |
| 75 | 3-chlorobenzyl | yellow | 118.5 – 119 |
| 76 | 4-ethoxybenzyl | bright yellow | 118 – 118.5 |
| 77 | 1-methyl-2-(methylthio)ethyl | yellow | 58 – 60 |
| 78 | 4-butoxybenzyl | | |
| 79 | 2-(methylthio)propyl | yellow | 34 – 36 |
| 80 | 4-(1,1-dimethyl)ethylbenzyl | yellow | 101 – 102 |
| 81 | 4-(hexyloxy)benzyl | yellow | 70.5 – 71.5 |
| 82 | 3-butoxybenzyl | yellow | 55 – 56 |
| 83 | 3-methoxybenzyl | yellow | 77 – 78 |
| 84 | 4-(1-methylpropoxy)benzyl | pale yellow | 54 – 55 |
| 85 | 4-ethylbenzyl | pale yellow | 60 – 61 |
| 86 | 4-benzyloxybenzyl | tan | 107 – 108 |
| 87 | 4-(2-propynyloxy)benzyl | pale yellow | 99 – 101 |

Compounds of this invention exhibit useful insecticidal activity being of particular interest for control of the larvae "caterpillar" or "worm" forms of insects of the genus Heliothis, such as *H. Zea* (corn earworm, cotton bollworm, tomato fruitworm), *H. virescens* (tobacco budworm); the genus Agrotis, such as *A. ipsilon* (Black cutworm); the genus Trichoplusia, such as *T. ni* (cabbage looper), and the genus Spodoptera, such as *S. littoralis* (Egyptian cotton leafworm). Some are also of interest for controlling aphids, whiteflies and houseflies. In tests that have been conducted they have exhibited low, or no, toxicity to other insects such as the 2-spotted spider mite and mosquito larva. Some act very rapidly providing "quick knock-down" of insects; in some cases even though the compound is not very toxic to the insects.

Activity of compounds of this invention with respect to insects was determined by using standardized tests to establish the LC$_{50}$ dosage (in milligrams of test compound per 100 milliliters of solvent or liquid carrier required in the solution or suspension of test compound used) that was required to kill 50% of the test insects. The test insects were the housefly, corn earworm, pea aphid and 2-spotted spider mite, and in some cases, the black cutworm. Activity with respect to mosquito larvae was determined by placing the larvae in water containing the test compound.

All of compounds 1 though 87 were found to be inactive or but slightly active with respect to the mites and mosquito larvae. With respect to the corn earworm, all of the compounds were found to be active. With respect to the pea aphid, compounds 3, 6, 8–11, 14–16, 18, 20, 27–30, 32, 34, 36, 39–42, 44, 46, 49–50, 52–57, 59–62, 66, 68, 70, 76–79, 84 and 87 were found to be active. With respect to the housefly, compounds 1-3, 5–11, 14–25, 27–30, 32, 34, 36, 39–42, 44, 46, 48–50, 52–54, 56–57, 59–60, 62, 63, 70, 72, 73, 76, 78, 79, 81, 82 and 84–87 were found to be active. Compounds 1-3, 6–8, 10, 11, 14, 16–18, 27 and 29 were active with respect to the black cutworm.

In the course of these tests it was noted that compounds 11, 14, 18, 44, 52, 53 and 70 acted very quickly on houseflies, compounds 11, 18, 20, 39–42, 44, 49, 52, 76, 84 and 87 acted very quickly upon pea aphids and compounds 1, 5, 7–9, 11, 14–18, 20–24, 26–36, 39–42, 44–46, 48–50, 53, 56–61, 64–66, 68, 70, 77, 79, 85 and 87 acted very quickly upon corn earworm.

The invention includes within its scope insecticidal compositions comprising an adjuvant — that is, a carrier optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as for example, coumarone resins, polyvinyl chloride and styrene polymers and copolymers; solid polychlorophenols; bitumen, waxes such as beeswax, paraffin wax and chlorinated mineral waxes; degradable organic solids such as ground corn cobs and walnut shells, and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons, such as benzene, toluene and xylene; petroleum fractions, such as kerosene, light mineral oils, chlorinated hydrocarbons, such as carbon tetrachloride, perchlorethylene trichloroethane, including liquefied normally vaporous gaseous compounds. Mixtures of different liquids are often suitable.

If used, the surface-active agent may be an emulsifying agent or a dispensing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e., the dosage to which the insect contacts — is of the order of 0.001% to 0.5% based on the total weight of the formulation, though under some circumstances the effective concentration will be as little as 0.0001% or as much as 2%, on the same basis.

I claim as my invention:

1. A method of killing insects which comprises contacting them with an insecticidally effective amount of a resonance hybrid in which the significant forms are represented by the formulae

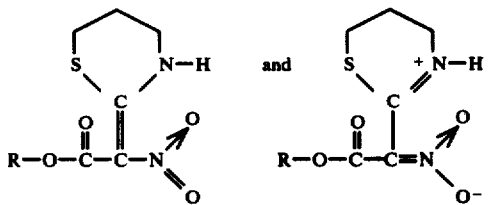

and the enol form represented by the formula

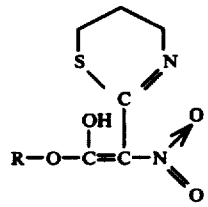

wherein R contains up to thirty carbon atoms and is alkyl, alkenyl, alkynyl, cycloalkyl, cycloalkylalkyl, alkadienyl, haloalkyl, haloalkenyl, mono- and poly-(alkoxy)alkyl, alkylthioalkyl, phenylthioalkyl, benzylthioalkyl, cyanoalkyl, hydroxyalkyl, alkylsulfinylalkyl, alkylsulfonylalkyl, phenyl or phenalkyl or either substituted on the ring by one to two of one or more of halogen, nitro, cyano, alkyl, phenyl, alkoxy or phenoxy; is aminoalkyl, $-(CH_2)_m-NR^3R^4$, wherein $m$ is one or two, $R^3$ is alkyl, cycloalkyl, alkenyl, phenyl or phenalkyl, and $R^4$ is hydrogen or one of the moieties represented by $R^3$; or is $-(CH_2)_n-R^5$, wherein $n$ is zero, one or two, and $R^5$ is a heteromonocyclic moiety with from five to six atoms in the ring, containing carbon atoms and one to two oxygen (—O—), sulfur (—S—) or nitrogen atoms (=N— or —NH—) bonded to carbon in the ring.

2. An insecticidal composition comprising an insecticidally effective amount of the compound defined in claim 1 together with a pesticide carrier and optionally a surface-active agent.

* * * * *